United States Patent [19]

Chiou

[11] Patent Number: 5,198,454
[45] Date of Patent: Mar. 30, 1993

[54] USE OF OB-104 TO TREAT OCULAR INFLAMMATION

[75] Inventor: George C. Y. Chiou, College Station, Tex.

[73] Assignee: Texas A&M University System, College Station, Tex.

[21] Appl. No.: 801,890

[22] Filed: Dec. 3, 1991

[51] Int. Cl.$^5$ .......................................... A61K 31/425
[52] U.S. Cl. .................................. 514/369; 514/912; 424/427
[58] Field of Search ............... 514/369, 912; 424/427, 424/429

[56] References Cited

U.S. PATENT DOCUMENTS 3,896,223  7/1975  Ariyan et al. ................ 514/370

FOREIGN PATENT DOCUMENTS 57-171986  4/1981  Japan ................................ 514/370

OTHER PUBLICATIONS

Remington Pharmaceutical Sciences, fifteenth edition (1975), pp. 1491–1492.
Polansky et al., "Anti-Inflammatory Agents: Steriods as Anti-Inflammatory Agents", Sears, Ed., *Handbook of Experimental Pharmacology* Springer-Verlag, (1985) 69:459–538.
Miyano et al., *Opthalmic Res.* (1984) 16:256–263.
Chiou et al., *J. Ocular Pharmacol.* (1985)1(4):383–389.
Bhattercherjee et al., "Effects of Lipooxygenase Products on Leukocyte Accumulation in the Rabbit Eye" Samuelsson et al., Eds., *Leukorienes and Other Lipooxygenase Products* Raven Press (1982) pp. 325–330.
Chang et al., *J. Ocular Pharmacol.* (1989) 5(4):353–360.

*Primary Examiner*—Frederick E. Waddell
*Assistant Examiner*—Zohreh A. Fay
*Attorney, Agent, or Firm*—Morrison & Foerster

[57] ABSTRACT

A novel compound for the treatment and prevention of ocular inflammation is disclosed. The compound, OB-104, is effective at both the early and late phases of inflammation.

9 Claims, 4 Drawing Sheets

USE OF OB-104 TO TREAT OCULAR INFLAMMATION

TECHNICAL FIELD

The present invention relates generally to the treatment and prevention of ocular inflammation. More specifically it relates to a novel compound shown to be an effective ocular antiinflammatory agent.

BACKGROUND OF THE INVENTION

Inflammation may occur in the eye following ocular surgery. Steroidal and nonsteroidal antiinflammatory agents (NSAIAs) have been used to relieve the inflammation. However, steroidal agents can induce an increase in intraocular pressure (Polansky et al., "Antiinflammatory Agents", in Sears, ed., *Handbook of Experimental Pharmacology*, Springer-Verlag, (1985), 69:459-538). The NSAIAs, such as salicylates, phenylbutazone, indomethacin, ibuprofen and naproxen, can produce numerous side effects, including edema, nausea, stomatitis, epigastric pain, peptic ulcer, agranulocytosis, hepatitis and drug rash. In addition, the NSAIAs may actually worsen the inflammation, especially during the late phase of the inflammation. This is because the clinically available NSAIAs at this time are primary cyclooxygenase inhibitors. Blocking the cyclooxygenase arm of the arachidonic acid (AA) cascade potentiates the production of lipooxygenase metabolites which are ultimately the leukotrienes (LT). LTs are responsible for the late phase of inflammation and for the chemotaxis of leukocytes (Miyano et al., *Ophthalmic Res.* (1984) 16:256-263; Chiou et al., *J. Ocular Pharmacology* (1985) 1:383-389; Bhattercherjee et al., "Effects of lipooxygenase products on leukocyte accumulation in the rabbit eye' in Samuelsson et al., eds., *Leukotrienes and Other Lipoxygenase Products*, Raven Press (1982) 325-330.) A previous study indicated that a new synthetic lipooxygenase inhibitor, REV 5901, was effective in reducing the late phase of inflammation. However, when REV 5901 was used alone in treatment of lens protein induced ocular inflammation, there was an increase in the early phase of inflammation. This observation was attributed to an increase in the production of prostaglandins caused by the inhibition of the lipooxygenase arm of the AA cascade. (Chang et al., *J. Ocular Pharmacology*, (1989) 5:353-360). The early phase of the inflammation has been effectively suppressed by indomethacin.

DISCLOSURE OF THE INVENTION

The present invention relates to a method for the prevention and treatment of ocular inflammation. In one embodiment, the invention is drawn to the use of a new agent, OB-104, as an ocular antiinflammatory agent.

The formula of this compound is as follows:

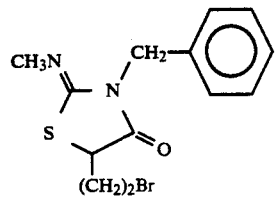

In a second embodiment, the invention involves a pharmaceutical preparation for use in the prevention and treatment of ocular inflammation which comprises the above compound in admixture with a pharmaceutically acceptable excipient.

DETAILED DESCRIPTION OF THE INVENTION

Figure 1:
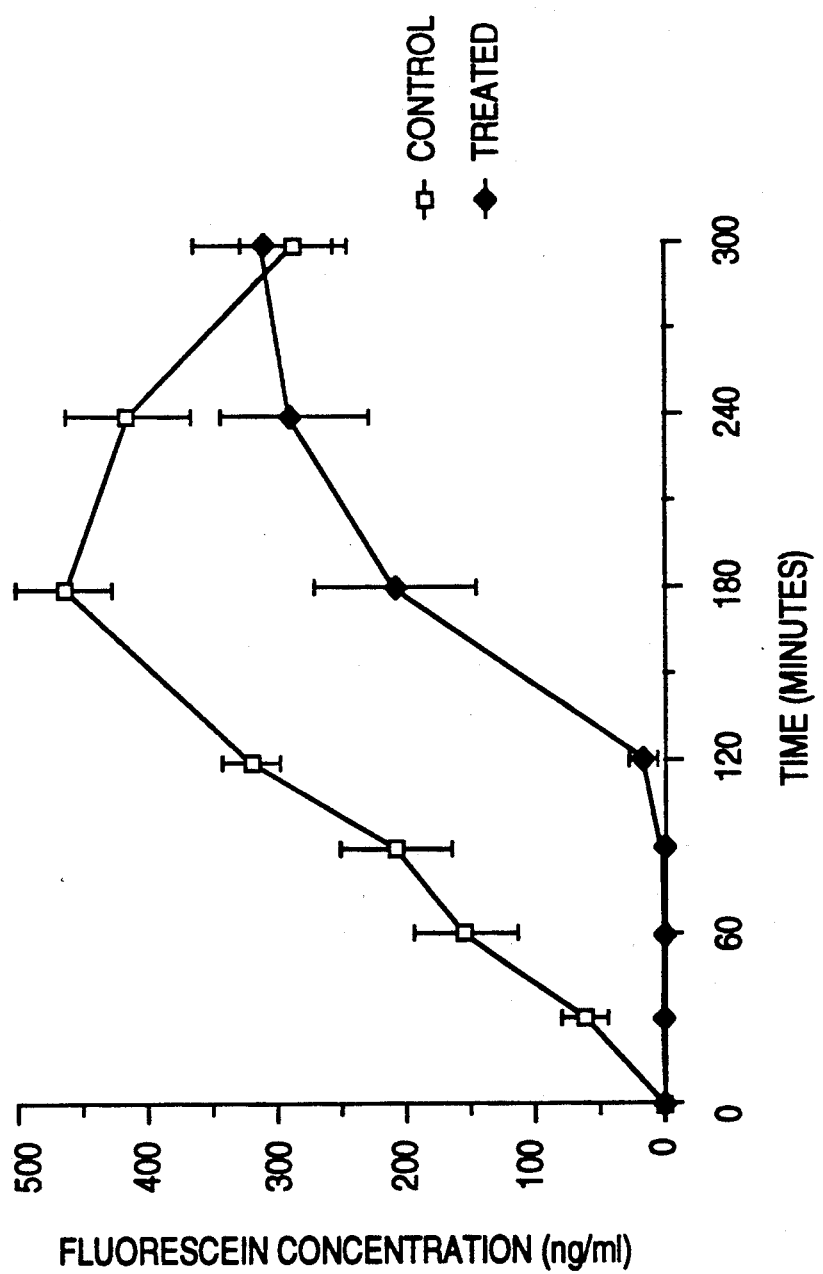
FIG. 1 shows a comparison of the effects of 1% indomethacin on ocular inflammation induced by lens protein injected intracamerally to that of a control that received no drug. Each point is a mean of 9 values for fluorescein concentration in the anterior chamber of the eye. The bars represent the standard error of the mean ("SEM").

The present invention is applicable to ocular inflammation at both the early and late phases of inflammation. OB-104 has been tested for suppression of ocular inflammation and been found to reduce inflammation induced in the iris, the ciliary body and the retina.

Definitions

In this specification and in the claims which follow, reference will be made to a number of terms which shall be defined to have the following meanings:

"Treatment" as used herein refers to the reduction or elimination of inflammation (therapy).

"Prevention" refers to the treatment of surgical patients to avoid inflammation (prophylaxis).

"Inflammation-controlling effective amount" refers to the amount of the pharmaceutically active substance sufficient to elicit at least a desired threshold response to the substance in a subject to which the substance is administered, whether therapeutic or prophylactic.

"Pharmaceutically active substance" as used herein refers to a substance that has been shown to be useful in the treatment of ocular inflammation. In the present invention, pharmaceutically active substances include OB-104, indomethacin, REV 5901, and prednisolone.

"Pharmaceutical composition" refers to a composition containing the pharmaceutically active substance. The composition may also contain a pharmaceutically acceptable vehicle.

Process for Preparation

OB-104 may be prepared according to the methods described in Okawara et al. *Chem. Pharm. Bull* 34(1) 380–384 (1986). The synthesis scheme is described in Example 1 below.

Administration

The administration of OB-104 described herein can be via any of the accepted modes of administration of pharmaceutical compositions. These methods include topical administration of solutions, suspension ointments or gels, parenteral injection, or oral administration.

Depending on the intended mode of administration, the compositions may be in the form of solid, semi-solid or liquid dosage forms, such as for example, tablets, pills, capsules, powders, liquids, suspensions, or the like, preferably in unit dosage forms suitable for single administration of precise dosages. The compositions will include a conventional pharmaceutical vehicle and, in addition, may include other medicinal agents, pharmaceutical agents, carriers, adjuvants, diluents, etc. The amount of active compound administered will, of course be dependent on the subject being treated, the manner of administration and the judgment of the prescribing physician.

The conventional pharmaceutical vehicle should be compatible with the pharmaceutically active substance of the pharmaceutical composition. Suitable vehicles for ocular use are, for example, sterile isotonic solutions such as isotonic sodium chloride or boric acid solutions. These vehicles typically contain sodium chloride or boric acid, respectively, as well as benzalkonium chloride and sterile distilled or purified water. Also useful is phosphate buffered saline (PBS), pH 7.4. Other suitable vehicular constituents include phenylmercuric nitrate, sodium sulfate, sodium sulfite, disodium phosphate and monosodium phosphate.

The compositions may also contain auxiliary substances i.e. antimicrobial agents such as chlorobutanol, parabans or organic mercurial compounds; pH adjusting agents such as sodium hydroxide, hydrochloric acid or sulfuric acid; and viscosity increasing agents such as methylcellulose. One of ordinary skill in the art will easily find substitutions for the above auxiliary substances. The final composition should be sterile, essentially free of foreign particles, and have a pH that allows for optimum drug stability. Generally pH values in the range of 5–8 will find use with the subject composition. Preferably, the pH will be as close to the pH of tear fluid, i.e. 7.4, as possible.

Typically the compositions of the subject invention are prepared as solutions, suspensions, ointments, gels, or ocular delivery devices such as drug-impregnated solid carriers that are inserted into the eye. If such a carrier is used, the above-mentioned vehicles are unnecessary. A variety of polymers can be used to formulate ophthalmic drug carriers. Saettone, M. F., et al., *J. Pharm. Pharmacol.* (1984) 36:229, and Park, K. et al., in *Recent Advances in Drug Delivery Systems*, Anderson et al, eds., Plenum Press (1984) 163–183, describe such polymers, the disclosures of which are incorporated herein by reference in their entirety. Drug release is generally effected via dissolution or bioerosion of the polymer, osmosis, or combinations thereof. The device should be formulated to release the drug at a rate that does not significantly disrupt the tonicity of tear fluid.

More specifically, several matrix-type delivery systems can be used with the subject invention. These systems are described in detail in Ueno et al., "Ocular Pharmacology of Drug Release Devices", in *Controlled Drug Delivery*, Bruck, ed., vol. II, Chap 4, CRC Press Inc. (1983), the disclosure of which is incorporated herein by reference in its entirety. Such systems include hydrophilic soft contact lenses impregnated or soaked with the desired drug, as well as biodegradable or soluble devices that need not be removed after placement in the eye. These soluble ocular inserts can be composed of any degradable substance that can be tolerated by the eye and that is compatible with the drug to be administered. Such substances include but are not limited to poly(vinyl alcohol), polymers and copolymers of polyacrylamide, ethylacrylate, and vinylpyrrolidone, as well as cross-linked polypeptides or polysaccharides, such as chitin.

Capsule-type delivery systems will also find use with the instant invention. These systems, described in Ueno et al., supra, utilize polymer membranes to control the release of the drug in question. These devices are particularly useful for the delivery of hydrophilic drugs. Hydrophobic drugs can be administered via a silicone rubber device such as described in Ueno et al., supra.

Ophthalmic ointments will include a base, generally composed of white petrolatum and mineral oil, often with anhydrous lanolin. Polyethylene-mineral oil gel is also satisfactory, as are other substances that are non-irritating to the eye, permit diffusion of the drug into the ocular fluid, and retain activity of the medicament for a reasonable period of time under storage conditions. If suspensions are used, the particle sizes therein should be less that 10 $\mu$m to minimize eye irritation. Furthermore, if solutions or suspensions are used, the amount delivered to the patient should not exceed 50 $\mu$l, preferably 25 $\mu$l or less, to avoid excessive spillage from the eye.

For solid compositions, conventional nontoxic solids including, for example, pharmaceutical grades of mannitol, lactose, starch, magnesium stearate, sodium saccharin, talc, cellulose, glucose, sucrose, magnesium carbonate, and the like may be used. Liquid pharmaceutically administrable compositions can, for example be prepared by dissolving, dispersing, etc. an active compound as defined above and optional pharmaceutical adjuvants in a vehicle, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975.

For oral administration, i.e., of any of the present compounds which may be orally active, a pharmaceutically acceptable nontoxic composition is formed by the incorporation of any of the normally employed vehicles described above. Such compositions take the form of solutions, suspensions, tablets, pills, capsules, powders, sustained-release formulations and the like. Such compositions may contain 1%–95% active ingredient, preferably 1–10%. An inflammation-controlling effective amount for purposes of preventing or treating ocular inflammation is usually in the range of 1-50 mg/kg. In order to prevent inflammation in surgical patients, the compound should be administered prior to surgery. For example, the compound may be administered 2-15 hours prior to surgery. Preferably, the compound is administered in multiple doses every 2-6 hours for 10-15 hours prior to surgery. For best results, the compound is administered 12, 8, and 2 hours prior to surgery. Similarly, the compound, should, for best results, be administered following surgery in multiple doses. For example, the compound can be administered for 3-10 days post surgery every 4-8 hours. Preferably, the compound is administered every 6 hours following surgery for 5-7 days. In order to treat inflammation, the compound should be administered every 4-8 hours for 3-10 days. Preferably, the compound is administered every 6 hours for 5-7 days.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable vehicles are, for example, water, saline, dextrose, glycerol, ethanol or the like. In addition, if desired, the pharmaceutical compositions to be administered may also contain minor amounts of nontoxic auxiliary substances such as wetting or emulsifying agents, pH buffering agents and the like, such as, for example, sodium acetate, sorbitan monolaurate, triethanolamine oleate, etc. An inflammation-controlling effective amount for purposes of preventing or treating ocular inflammation is usually in the range of 0.1-20 mg/kg. The compound is administered as described above with regard to oral administration.

The subject compounds can also be administered by implantation of a slow-release or sustained-release system, such that a constant level of dosage is maintained. For a review of these sustained release systems see Ueno, et al., "Ocular Pharmacology of Drug Release Devices", in *Controlled Drug Delivery*, Bruck, ed., vol. II, Chap 4, CRC Press Inc. (1983). An inflammation-controlling effective amount for purposes of preventing or treating ocular inflammation is usually in the range of 0.1-20 mg/kg/day. The system can be implanted after surgery in order to prevent inflammation. In order to treat inflammation, a new implant is inserted every 3-10 days for up to 60 days. Preferably, a new implant is inserted every 5-7 days for up to 30 days.

Topical administration of OB-104 in the form of eyedrops was found to be effective in inhibiting anterior ocular inflammation induced by lens protein injected into the anterior chamber. These results indicate that OB-104 can cross the cornea barrier effectively to inhibit the inflammation inside the eyeball. An inflammation-controlling effective amount for purposes of preventing or treating ocular inflammation is usually in the range of 0.1-20 mg/kg. The compound is administered as described above with respect to oral administration.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

EXAMPLES

EXAMPLE 1

Synthesis of OB-104

This example describes the preparation of 5-bromoethyl-3-benzyl-2-methyliminothiazolidin-4-one (OB-104) according to Scheme 1.

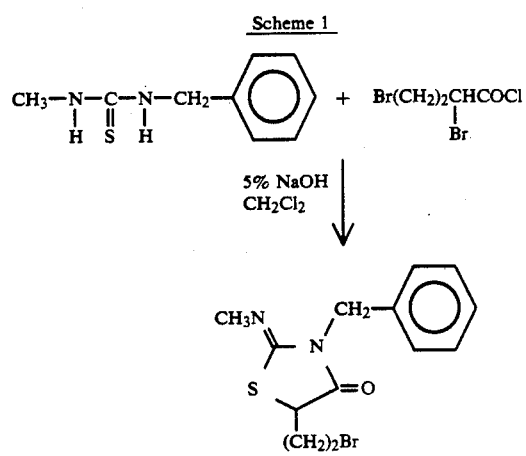

OB-104 can be synthesized as described in Okawara et al. *Chem. Pharm. Bull* 34(1) 380-384 (1986). Briefly, bromoacylchloride (5 mmol) is added dropwise to a stirred solution of 1-methyl-3-benzyl thiourea (5 mmol) in a solution of 5% sodium hydroxide (12 ml) and dichloromethane (20 ml). The solution is constantly cooled with ice-water. When the addition is over, the reaction mixture is stirred for 12 hours at room temperature. The $CH_2Cl_2$ layer is separated, washed with $H_2O$ (15 ml×2), dried over anhydrous $Na_2SO_4$ and evaporated to dryness. The residue is purified by recrystallization from EtOH or by silica-gel column chromatography ($CHCl_3$) to yield 5-bromoethyl-3-benzyl-2-methyliminothiazolidin-4-one (OB-104).

EXAMPLE 2

Effects of Various Compositions on Lens Protein Induced Inflammation

A. Materials

Indomethacin was purchased from Sigma (St. Louis, Mo.). REV 5901 was obtained from Revlon Health Care Group (Tuckahoe, N.Y.). A 1% ophthalmic solution of prednisolone (1% Econopred) was purchased from Alcon (Fort Worth, Tex.). OB-104 was obtained from Drs. M. Furukawa and T. Okawara at the University of Kumamoto. Indomethacin, REV 5901 and OB-104 were dissolved in polyethylene glycol (molecular weight 200) (60%) and then diluted with aqueous solution (40%) to a final concentration of 1%.

Fluorescein labeled dextran with molecular weight of 70,000 (FD 70) was obtained from Sigma. 100 mg of FD 70 was initially dissolved in phosphate buffer saline (Sigma) and passed through a PD 10 column (Pharmacia). This solution was then diluted with heparinized normal saline to make a final concentration of a vehicle of 10 mg/ml FD 70 and 100 U/ml of heparin.

Lens protein was prepared and protein concentration was determined according to procedures described in Miyano et al. *Ophthalmic Res.* (1984) 16:256-263. The quantity of lens protein in the lens protein preparation was 29.67 mg/ml.

B. Methods

New Zealand White albino rabbits of either sex weighing 2.0 to 3.0 kg were used. The rabbits were initially anesthetized with 25 mg/kg of ketamine and 5 mg/kg of xylazine given intramuscularly. Half of the above dosage was given hourly for the remainder of the experiment. 15 minutes after the anesthesia, 50 μl of the solvent was instilled into the right eye. 50 μl of drug solution was instilled into the left eye. One hour after the application of the drug and the vehicle, 24 μl of the lens protein was injected into the anterior chamber with a 30 gauge needle. Extreme care was taken to avoid traumatizing the iris. Fifteen minutes after the injection of the lens protein, FD 70 (1.4 mg/kg) was injected via a marginal ear vein. The rabbits were euthanized at the end of the experiment with an injection of 10 ml of air through the marginal ear vein.

Scanning of the eyes was done by the use of a fluorophotometer (Fluorotron Master, Coherent Corp., Palo Alto, Calif.). Measurements were done at 0, 30, 60, 90, 120, 180, 240, and 300 minute intervals. The measurements are reported in FIGS. 1-4 and are expressed in ng/ml of FD 70 in the anterior chamber.

C. Results

All data were analyzed with Student's t-test for two values and analysis of variance for more than two values. Each value was expressed as mean ± standard error of the mean. A p value of 0.05 or less was considered significant.

FIGS. 1-4 describe the effects of the various compounds on lens protein induced inflammation. The greater the permeability of fluorescein from the blood stream into the eye, the greater the degree of inflammation.

Figure 2:
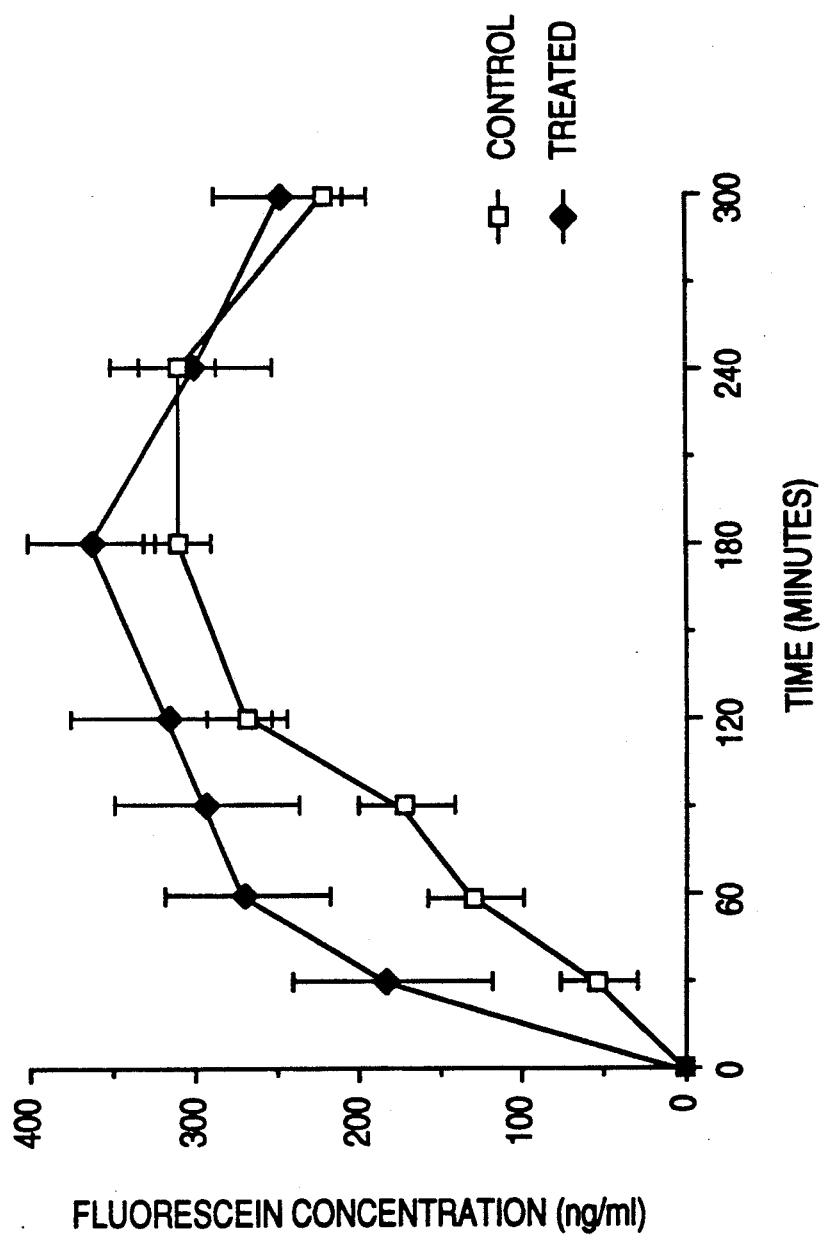
FIG. 2 depicts the effects of 1% REV 5901 on ocular inflammation induced by lens protein injected intracamerally as opposed to that of a control without the drug. Each point is a mean of 9 values for fluorescein concentration in the anterior chamber of the eye. The bars represent the SEM.
Figure 3:
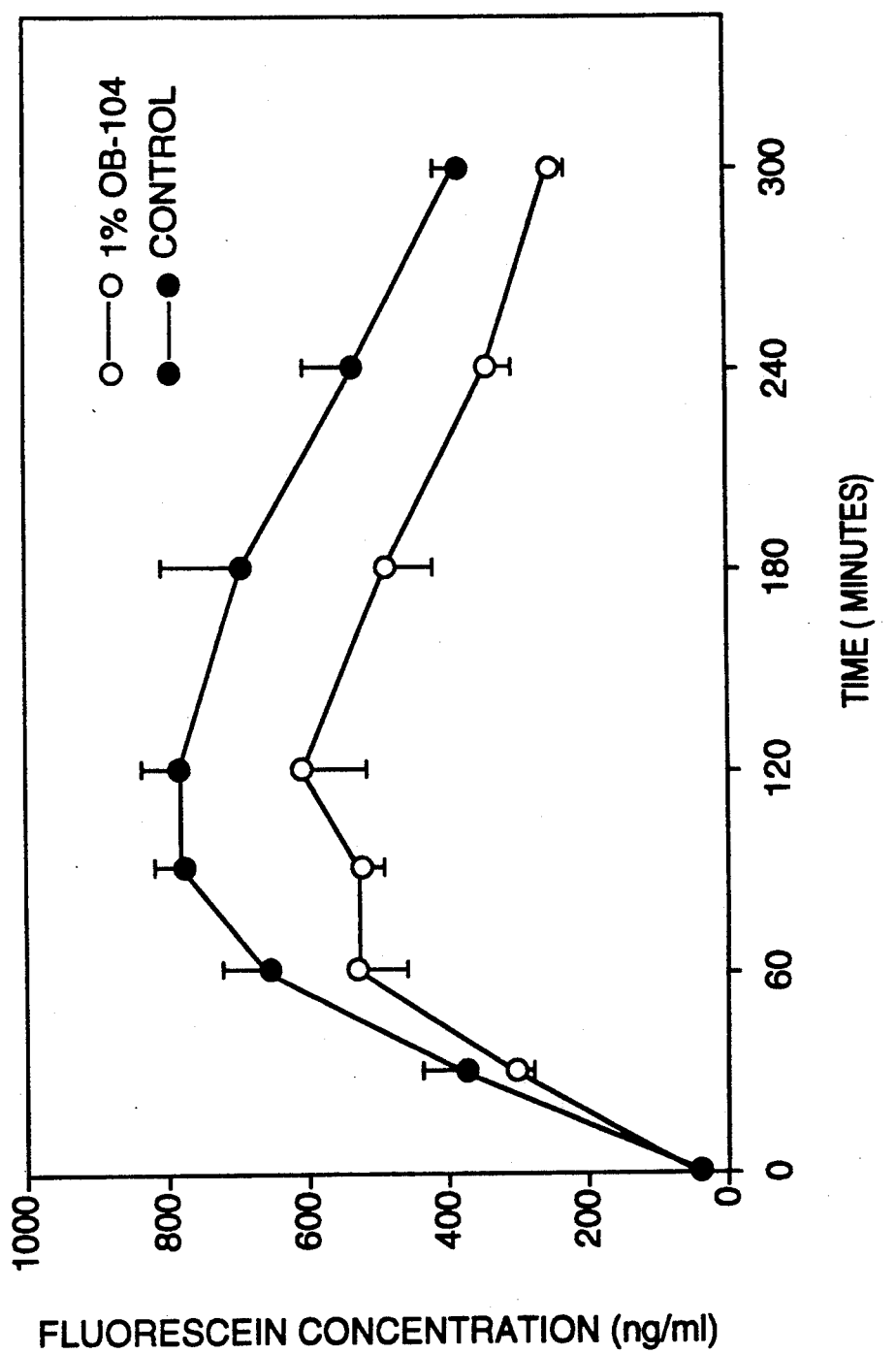
FIG. 3 shows a comparison of the effects of 1% OB-104 on ocular inflammation induced by lens protein injected intracamerally to that of a control that received no drug. Each point is a mean of 6 values for fluorescein concentration in the anterior chamber of the eye. The bars represent the SEM, and the asterisks indicate the significant difference from the corresponding control values at $p<0.05$.
Figure 4:
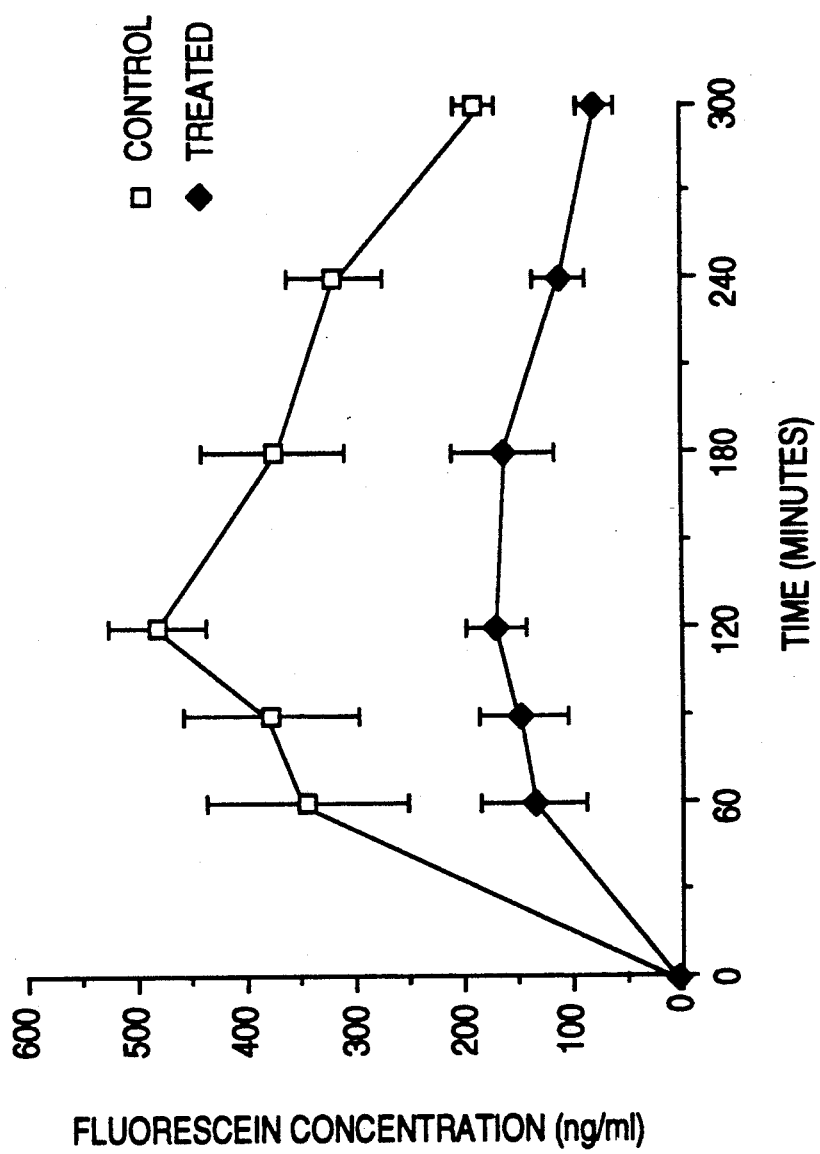
FIG. 4 depicts the effects of 1% prednisolone on ocular inflammation induced by lens protein injected intracamerally as opposed to that of a control without the drug. Each point is a mean of 5 values for fluorescein concentration in the anterior chamber of the eye. The bars represent the SEM.

The early phase of this lens protein induced inflammation (0-3 hours) was effectively suppressed by indomethacin but not the late phase (4-5 hours) (FIG. 1). On the other hand, REV 5901 reduced the late phase of inflammation but worsened the early phase (FIG. 2). OB-104 (FIG. 3) and prednisolone (FIG. 4) suppressed ocular inflammation at both the early and late phases of inflammation.

Modifications of the above described modes for carrying out the invention that are obvious to persons of skill in the art to which the invention pertains are intended to be within the scope of the following claims.

I claim:

1. A method for the treatment and prevention of ocular inflammation in an animal subject, which method comprises administering topically, orally, or parenterally to said animal subject an inflammation-controlling effective amount of a pharmaceutical composition comprising a pharmaceutically acceptable vehicle in admixture with a compound having the formula:

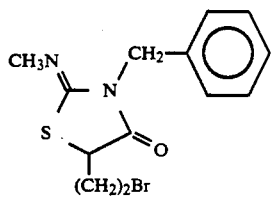

2. The method of claim 1 wherein the ocular inflammation is in the anterior portion of the eye.

3. The method of claim 1 wherein the compound is administered orally.

4. The method of claim 1 wherein the compound is administered parenterally.

5. The method of claim 1 wherein the compound is administered topically.

6. The method of claim 2 wherein the compound is administered topically.

7. A method for the treatment and prevention of ocular inflammation in an animal subject, which method comprises inserting an ocular delivery device into the eye of said animal subject, said ocular delivery device comprising an inflammation-controlling effective amount of a compound having the formula:

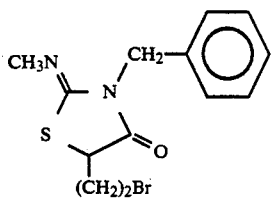

8. An ocular delivery device useful for the treatment and prevention of ocular inflammation comprising an effective amount of a compound having the formula:

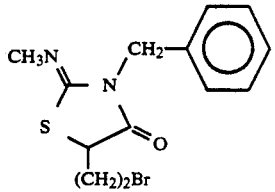

9. A pharmaceutical composition useful for the treatment and prevention of ocular inflammation in an animal subject comprising an effect amount of a compound having the formula:

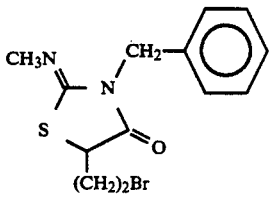

in admixture with a pharmaceutically acceptable vehicle.

* * * * *